(12) United States Patent
Carey et al.

(10) Patent No.: US 7,052,840 B2
(45) Date of Patent: May 30, 2006

US007052840B2

(54) REVERSIBLE ASSOCIATION OF NUCLEIC ACID WITH A CARBOXYLATED SUBSTRATE

(75) Inventors: Indira Carey, Silver Spring, MD (US); Teri Heiland, New Market, MD (US); Anna Smith, Gaithersburg, MD (US); Jill Ray, Rockville, MD (US)

(73) Assignee: Capitol Genomix, Inc., Gaithersburg, MD (US)

( * ) Notice: Subject to any disclaimer, the term of this patent is extended or adjusted under 35 U.S.C. 154(b) by 430 days.

(21) Appl. No.: 10/114,929

(22) Filed: Apr. 3, 2002

(65) Prior Publication Data

US 2003/0194707 A1 Oct. 16, 2003

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................................... 435/6; 435/91.2
(58) Field of Classification Search .................... 435/6; 536/23.1, 23.5
See application file for complete search history.

(56) References Cited

U.S. PATENT DOCUMENTS

| 4,554,088 | A | 11/1985 | Whitehead et al. ...... 252/62.54 |
| 4,628,037 | A | 12/1986 | Chagnon et al. ............ 436/526 |
| 4,672,040 | A | 6/1987 | Josephson ................... 436/526 |
| 4,682,195 | A | 7/1987 | Yilmaz ....................... 357/23.4 |
| 4,683,202 | A | 7/1987 | Mullis .......................... 435/91 |
| 4,695,393 | A | 9/1987 | Whitehead et al. ...... 252/62.54 |
| 4,698,302 | A | 10/1987 | Whitehead et al. ........... 435/94 |
| 4,774,265 | A | 9/1988 | Ugelstad et al. .............. 521/55 |
| 5,539,082 | A | 7/1996 | Nielsen et al. .............. 530/300 |
| 5,645,897 | A | 7/1997 | Andra ......................... 427/526 |
| 5,705,628 | A | 1/1998 | Hawkins |
| 5,705,629 | A | 1/1998 | Bhongle ................... 536/25.34 |
| 5,714,331 | A | 2/1998 | Buchardt et al. .............. 435/6 |
| 5,719,262 | A | 2/1998 | Buchardt et al. ............ 530/300 |
| 5,736,336 | A | 4/1998 | Buchardt et al. .............. 435/6 |
| 5,766,855 | A | 6/1998 | Buchardt et al. .............. 435/6 |
| 5,773,571 | A | 6/1998 | Nielsen et al. .............. 530/300 |
| 5,786,461 | A | 7/1998 | Buchardt et al. .......... 536/18.7 |
| 5,891,625 | A | 4/1999 | Buchardt et al. .............. 435/6 |
| 5,898,071 | A * | 4/1999 | Hawkins ..................... 536/25.4 |
| 5,908,845 | A | 6/1999 | Segev .......................... 514/261 |
| 6,221,600 | B1 | 4/2001 | MacLeod et al. ............... 435/6 |
| 6,310,199 | B1 | 10/2001 | Smith et al. ................ 536/25.4 |
| 2002/0042112 | A1* | 4/2002 | Koster et al. ................ 435/174 |

FOREIGN PATENT DOCUMENTS

| EP | 1 306 446 A1 * | 5/2003 |
| WO | 92/20702 | 11/1992 |
| WO | WO/02/012559 | * 2/2002 |

OTHER PUBLICATIONS

Birnboim, et al., "A Rapid Alkaline Extraction Procedure for Screening Recombinant Plasmid DNA," Nucleic Acids Res. Nov. 24, 1979; 7(6):1513-23.
Birnboim, "A Rapid Alkaline Extraction Method for the Isolation of Plasmid DNA," Methods Enzymol. 1983; 100:243-55.
Brisco, et al., "Clean Up the Competition," Promega Notes 2001; 79:18-21.
Cautrecasas, "Protein Purification by Affinity Chromatography," J. Biol. Chem., 245, 3059 (1970).
DeAngelis, et al., "Solid-Phase Reversible Immobilization for the Isolation of PCR Products," Nucleic Acids Res. Nov. 25, 1995;23(22):4742-3.
Eickbush, et al., "The Compaction of DNA Helices into Either Continuous Supercoils or Folded-Fiber Rods and Toroids," Cell. 13(2):295-306 (1978).
Horowicz and Burke, Rapid and Efficient Cosmid Cloning, Nucleic Acids Res. 9:2989 (1981).
Wang, et al., "Rapid Analysis of Gene Expression (RAGE) Facilitates Universal Expression Profiling," Nucleic Acids Res. 27(23):4609-4618 (1999).
Sambrook, et al., "Extraction and Purification of Plasmid DNA," Molecular Cloning: A Laboratory Manual 1989 (2nd ed.); Ch. 1:1-21-1.32.
Ausubel, et al., "Minipreps of Plasmid DNA," Current Protocols in Molecular Biology 1998; Ch. 1:1.6.1-1.6.10; Ch. 2:2.1.1-2.7.8.

* cited by examiner

*Primary Examiner*—W. Gary Jones
*Assistant Examiner*—Sally A. Sakelaris
(74) *Attorney, Agent, or Firm*—Vinson & Elkins L.L.P.

(57) ABSTRACT

The present invention is directed to methods and compositions wherein nucleic acids are associated with a solid phase that comprises a carboxylated substrate. In specific embodiments, precipitation of the nucleic acids occurs in the absence of salt.

25 Claims, 11 Drawing Sheets

Lane 1: Unprecipitated DNA
Lanes 2 and 3: Sodium Chloride
Lanes 4 and 5: Lithium Chloride
Lanes 6 and 7: Magnesium Chloride
Lanes 8 and 9: Ammonium Acetate
Lanes 10 and 11: Potassium Chloride

REVERSIBLE ASSOCIATION OF NUCLEIC ACID WITH A CARBOXYLATED SUBSTRATE

FIELD OF THE INVENTION

The present invention is directed to the field of molecular biology, particularly nucleic acid manipulation. More specifically, the present invention regards the reversible association of nucleic acids to a carboxylated substrate.

BACKGROUND OF THE INVENTION

Traditionally, nucleic acids have been precipitated by the addition of various salts and ethanol or isopropanol (Eickbush and Moudrianakis, 1978). Methods for binding nucleic acid to a solid substrate are also well known in the art. However, these methods have traditionally required the addition of salts or other compounds or the manipulation of pH that could adversely effect the downstream application of the isolated molecules or require additional purification steps.

Reversible DNA binding to carboxylated beads is described in U.S. Pat. Nos. 5,898,071 and 6,310,199. These patents detail methods for DNA purification using carboxylated encapsulated magnetic particles. However, the disclosed methods require precise adjustments of salt and polyethylene glycol concentrations ('071 patent) or pH ('199 patent). As is well known in the art, high salt and PEG contamination may adversely effect downstream applications of the isolated nucleic acid, mandating an additional purification step. Further, modifying the pH of a solution can adversely affect DNA structure. The instant invention overcomes the noted deficiencies in the art by providing methods and compositions for the rapid and efficient purification of nucleic acids in which contaminants such as salts and/or PEG are not present and in which pH is not significantly altered.

SUMMARY OF THE INVENTION

The present invention is directed to methods and compositions whereby nucleic acids (DNA, RNA, and/or polyamide nucleic acid (PNA)) are precipitated from solution onto a solid phase that comprises a carboxylated substrate. The disclosed methods and compositions are compatible with a number of applications, including circumstances in which a nucleic acid is to be isolated, purified, removed or separated from a formulation, solution, mixture or liquid phase. Exemplary protocols in which the disclosed method may prove useful include, but are not limited to: buffer exchange during multi-step enzymatic reactions; DNA fragment isolation from agarose or polyacrylamide gels; plasmid DNA recovery from a cleared lysate; removal of PCR™ primers (PCR™ clean-up); cDNA clean up after synthesis; and concentration of nucleic acid samples.

In an exemplary embodiment, a carboxylated substrate, such as, for example a carboxylated bead, is washed with ethanol and then resuspended in ethanol. An effective amount of glycogen to precipitate DNA is added to a sample containing the DNA to be precipitated. The DNA sample/glycogen mixture is combined with the bead/ethanol slurry and incubated for about 15 min. Following the incubation, the beads are pelleted by centrifugation or, in the case of paramagnetic beads, concentrated with a magnet. The supernatant is then removed and discarded. The precipitated material on the beads may then be further washed with an ethanol solution to remove potential impurities, such as residual salts. The nucleic acid may be recovered from the beads by solubilization in a standard solution such as water or a suitable buffer such as 10 mM Tris, 1 mM EDTA, pH 8.0.

The instant disclosure conveys a number of embodiments relating methods or compositions encompassing the instant invention. A first embodiment involves a method of isolating nucleic acid, comprising contacting a composition comprising nucleic acid with an effective amount of glycogen to facilitate precipitation of nucleic acid and ethanol in the presence of a carboxylated paramagnetic bead. In this embodiment, such contact results in the association of the nucleic acid with the carboxylated paramagnetic bead. This embodiment may further incorporate the subsequent elution of the nucleic acid from the paramagnetic bead. This embodiment may further be carried out in the substantial absence of salt. As disclosed, this embodiment may be carried out at a variety of concentrations of glycogen. Specific embodiments may be carried out where an effective amount of glycogen comprises from about 1 µg/mL to about 1000 µg/mL, from about 200 µg/mL to about 500 µg/mL or about 250 µg/mL.

The invention as disclosed, is capable of separating, isolating and/or purifying a variety of nucleic acid forms. In specific embodiments, such nucleic acids may be DNA, including, but not limited to, genomic DNA, plasmid DNA or oligonucleotide. In alternate embodiments, the nucleic acid may be RNA. Further, association, isolation, separation and purification within the context of the invention is apparently not dependent upon size structure or conformation of the nucleotides. Thus, nucleic acids of lengths including, but not limited to 1–100 nucleotides, 100–1000 nucleotides, 1000–10,000 nucleotides and 10,000–1,000,000 nucleotides may be associated with a carboxylated substrate.

A further embodiment comprises a method for isolating nucleic acid, comprising contacting a composition comprising nucleic acid with an effective amount of glycogen to facilitate precipitation of nucleic acid and ethanol in the presence of a carboxylated substrate. In this embodiment, such contact results in the association of the nucleic acid with the carboxylated substrate. A related embodiment includes the subsequent elution of the nucleic acid from the carboxylated substrate. These embodiments may also be carried out in the substantial absence of salt.

The methods and compositions of the instant invention may be further comprised as a kit. In such an embodiment, a kit for nucleic acid isolation comprises, in a suitable containing means, at least a carboxylated substrate and a binding solution containing glycogen.

Embodiments of the instant invention may be further characterized as a composition for reversibly binding nucleic acid to a carboxylated substrate. Such a composition could comprise ethanol, a nucleic acid, and an effective amount of glycogen to facilitate precipitation of nucleic acid and a carboxylated substrate. Disclosed compositions may further substantially lack salt. Further, in such compositions, the carboxylated substrate may be a paramagnetic bead.

It is further contemplated that the methods and compositions of the instant invention may be carried out by an instrument. In such an embodiment, an instrument for isolating nucleic acid might comprise a means for contacting a composition comprising nucleic acid with ethanol and an effective amount of glycogen to facilitate precipitation of nucleic acid in the presence of a carboxylated substrate, wherein said contact results in the association of the nucleic acid with the carboxylated substrate. In an alternate embodiment, such an instrument isolating nucleic acid might comprise a means for containing a nucleic acid sample, a means for adding ethanol to the nucleic acid sample, a means for adding glycogen to the nucleic acid sample in an amount effective to cause precipitation of the nucleic acid and a carboxylated substrate in contact with the nucleic acid sample. In related embodiments, instruments may further include a plate containing individual wells, a holder for a plate containing individual wells, a holder for centrifuge tubes and/or a means for removing the carboxylated substrate from the sample. Where the instrument includes a means for removing the carboxylated substrate from the sample, this means may be by way of an electric field. In addition, the instrument may be designed to facilitate nucleic acid association where the carboxylated substrate is the inner surface of a centrifuge tube.

Other and further objects, features and advantages would be apparent and eventually more readily understood by reading the following specification and by reference to the accompanying drawing forming a part thereof, or any examples of the presently preferred embodiments of the invention given for the purpose of the disclosure.

BRIEF DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

In FIG. 1A, 1 to 50 ug of DNA was precipitated and recovered. Assuming 100% recovery, aliquots of recovered DNA estimated to be 500 ng were electrophoresed alongside 500 ng of non-precipitated plasmid DNA. Bands from precipitated samples were compared to non-precipitated controls using densitometry. These values were then used to calculate the amount of DNA in bands from precipitated samples and a percent recovery calculated. In FIG. 1B, 100 to 500 ng of DNA was precipitated and recovered. Assuming 100% recovery, aliquots of recovered DNA estimated to be 100 ng were electrophoresed alongside 100 ng of non-precipitated plasmid DNA. Percent recovery was calculated as in FIG. 1A.

FIG. 2 Recovery of small fragments from solution. One µg of a DNA ladder containing a mixture of fragments (25 bp to 300 bp) was precipitated onto carboxylated magnetic beads. Assuming 100% recovery, an aliquot of the recovered material (P) estimated to be 200 ng was electrophoresed on an 8% polyacrylamide gel next to 200 ng of non-precipitated ladder (C). The gel was stained with a 1/10,000 dilution of SYBR® Green 1 in 1×TBE and visualized using a Fluorimager. Recovery was assessed using densitometry as described in FIG. 1, and percent recovery reported as shown. Data is shown for 25 bp–150 bp fragments.

FIG. 3 Recovery of small double stranded DNA fragments from polyacrylamide gels. Approximately 200 ng of a 50 bp and a 200 bp fragment were excised from an 8% polyacrylamide gel. The gel slices were crushed and soaked in Binding Buffer at 65° C. for 4 h. The eluate was then precipitated onto carboxylated beads. Four µL of recovered material was electrophoresed alongside 3 different volumes [0.25 µL (M1), 0.5 µL (M2) and 1 µL (M3)] of a DNA quantitation ladder on an 8% polyacrylamide gel. The gel was stained with a 1/10,000 dilution of SYBR® Green 1 in 1×TBE and visualized using a Fluorimager. Recovery was assessed using densitometry by comparing bands from recovered DNA to bands of equivalent intensity on the quantitation ladder, and a percent recovery calculated.

FIG. 4 Recovery of DNA fragments from agarose gels. Approximately 300 ng of a 500 bp and a 1 kb fragment were excised from a 1% low melting temperature agarose gel. The slices were weighed and melted at 70° C. for 10–15 min., and then placed at 42° C. for 5 min. One unit Agarase/100 mg of agarose was added to the molten slices, which were then digested at 42° C. for 30 min. The digested material was precipitated onto carboxylated beads. Two µL of recovered material was electrophoresed alongside 1 µL of a DNA quantitation ladder (Marker) on a 1% agarose gel containing 0.5 µg/mL ethidium bromide. The gel was visualized using a Fluorimager. Recovery was assessed using densitometry by comparing bands from recovered DNA to bands of equivalent intensity on the quantitation ladder, and percent recovery calculated.

FIG. 5 The use of carboxylated beads for Buffer Exchange. Five µg of pBSTK (in duplicate) was digested with 20 units of XmnI at 37° C. for 1 h. The digested material was precipitated onto carboxylated magnetic beads and recovered. An aliquot of this material (approximately 1 µg) was then digested with 20 units of KpnI at 37° C. for 1 h, and visualized on a 1% agarose gel (containing 0.5 µg/mL ethidium bromide) using a Fluorimager. Shown is undigested plasmid (Control), XmnI-digested plasmid (XmnI), and the double-digested plasmid XmnI/KpnI).

FIG. 6 The use of carboxylated beads for cDNA clean-up and RAGEtag preparation. In FIG. 6A, cDNA made from the MCF-7 human breast cancer cell line was precipitated onto magnetic beads and recovered. One ng cDNA was used to amplify the 3' and 5' end regions from a panel of four housekeeping genes (clathrin, ARF F1, actin and GAPDH). In FIG. 6B, cDNA purified as in FIG. 6A was used to prepare RAGEtags for GS320™ (a PCR™ based gene profiling assay) analysis. RAGEtags were sequentially digested using DpnII and Hsp92II restriction enzymes. The digested material was precipitated onto carboxylated magnetic beads and recovered. Universal linkers were ligated and samples recovered and normalized. Normalized RAGEtags from four different samples (H1–H4) were amplified with the appropriate primer pair for TGF-β3. The PCR reactions were visualized on an 8% polyacrylamide gel stained with SYBR® Green 1 (1/10,000 dilution in 1×TBE) using a Fluorimager. TGF-β3 downregulation in H1, H2 and H4 compared to H3 is shown.

FIG. 7 Recovery of plasmid DNA from a cleared lysate. One and one-half mL (in duplicate) of an overnight culture of pBSTK (Bluescript plasmid) was lysed and cleared by the alkaline lysis method. Three µL 20 mg/mL glycogen was added to each lysate and the DNA recovered by precipitation onto carboxylated magnetic beads. Five µl of the plasmid solution was digested with 20 units of EcoRI at 37° C. for 1 h. The digested material (D) was electrophoresed on a 1% agarose gel (containing 0.5 µg/mL ethidium bromide) next to 5 µL of an undigested sample (U). Visualization was done using a Fluorimager.

FIG. 8 Recovery of total RNA using carboxylated beads. Five µg total Mouse Liver RNA was precipitated onto carboxylated magnetic beads and recovered. One µg of the recovered samples (P) was electrophoresed on a 1% agarose/ formaldehyde gel next to 1 μg of non-precipitated RNA (C). The gel was visualized using a Fluorimager.

Figure 9:
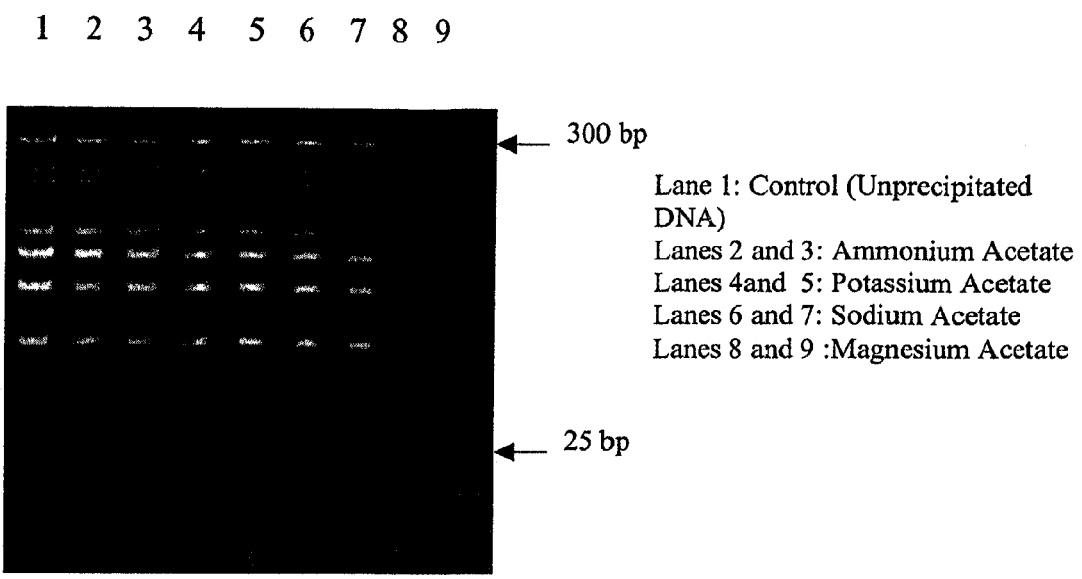

FIG. 9 DNA precipitation with acetate salts. One μg of a DNA ladder containing a mixture of fragments (25 bp to 300 bp) was precipitated onto carboxylated magnetic beads using a final 3.3 M concentration of various acetate salts. Assuming 100% recovery, aliquots (Lanes 3–9) of the recovered material estimated to be 200 ng were electrophoresed on an 8% polyacrylamide gel next to 200 ng of non-precipitated ladder (Lanes 1–2). The gel was stained with a 1/10,000 dilution of SYBR® Green 1 in 1×TBE and visualized using a Fluorimager.

Figure 10:
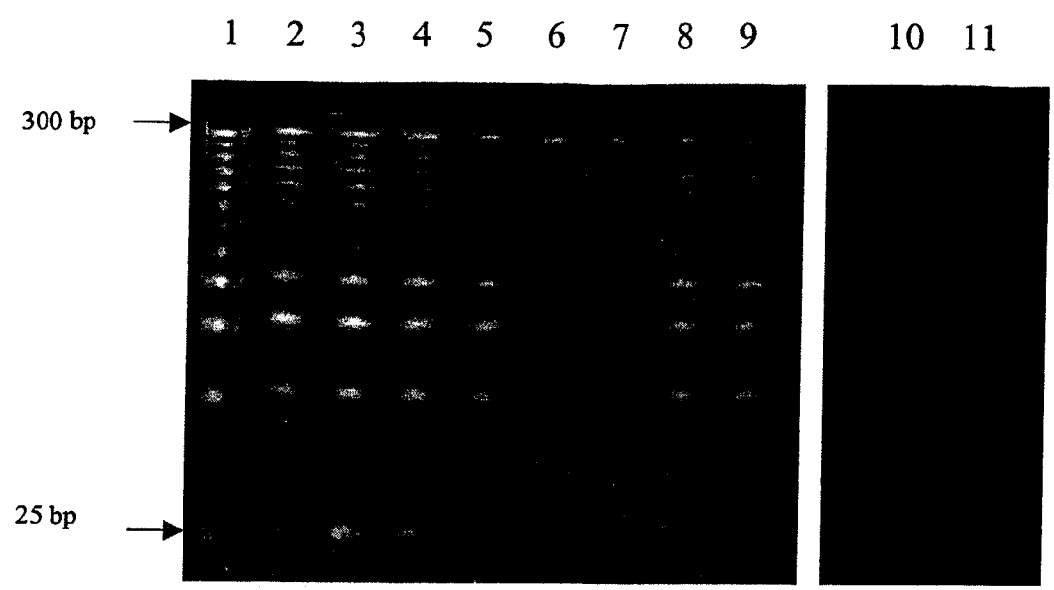

FIG. 10 DNA precipitation with chloride salts. One μg of a DNA ladder containing a mixture of fragments (25 bp to 300 bp) was precipitated onto carboxylated magnetic beads using a final 3.3 M concentration of various chloride salts. A sample precipitated with ammonium acetate was also included for comparison. Assuming 100% recovery, aliquots (Lanes 3–11) of the recovered material estimated to be 200 ng were electrophoresed on an 8% polyacrylamide gel next to 200 ng of non-precipitated ladder (Lanes 1–2). The gel was stained with a 1/10,000 dilution of SYBR® Green 1 in 1×TBE and visualized using a Fluorimager.

Figure 11:
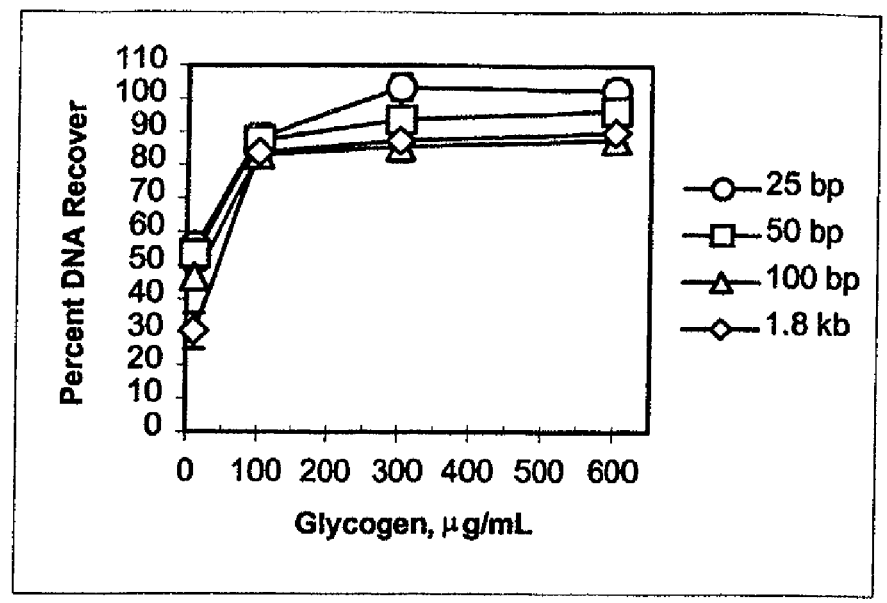

FIG. 11 Glycogen Titration. One μg of a DNA ladder containing a mixture of fragments (25 bp-1.8 kb) was precipitated with increasing concentrations of glycogen (10 μg/mL, 100 μg/mL, 300 μg/mL and 600 μg/mL) onto carboxylated magnetic beads, in the absence of salt. Assuming 100% recovery, aliquots of recovered DNA estimated to be 200 ng were electrophoresed on an 8% polyacrylamide gel next to 200 ng of non-precipitated ladder. The gel was stained with a 1/10,000 dilution of SYBR® Green 1 in 1×TBE and visualized using a Fluorimager. Bands from precipitated samples were compared to non-precipitated controls using densitometry. These values were then used to calculate the amount of DNA in bands from precipitated samples and a percent recovery calculated. Percent recovery is reported for selected fragments.

DETAILED DESCRIPTION OF THE INVENTION

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

I. Definitions

As used herein the specification, "a" or "an" may mean one or more. As used herein in the claim(s), when used in conjunction with the word "comprising", the words "a" or "an" may mean one or more than one. As used herein "another" may mean at least a second or more.

The term "carboxylated substrate" as used herein refers to a substrate having at least one carboxyl (COOH or COO—) group on its surface.

The term "association" refers to a noncovalent interaction between molecules, such as, for example between a nucleic acid and a carboxyl group. Noncovalent interactions include, for example, ionic, hydrophobic and hydrogen bonds.

II. The Present Invention

The present invention is directed to methods and compositions for the precipitation of nucleic acids, such as DNA, RNA, and/or PNA, using a carboxylated substrate. The disclosed methods and compositions utilize a single, simplified associating mixture that allows a nucleic acid to be reversibly associated with a carboxylated substrate and subsequently eluted with high yields. This association has not been found to be sequence or size dependent. The disclosed compositions and methods facilitate recovery of fragments in sizes ranging from 25 bp or less to genomic DNA with essentially equivalent efficiency. Further, nucleic acid molecules are associated with the carboxylated substrate reversibly and non-specifically.

An exemplary protocol employing compositions and methods as disclosed herein is as follows:

1) A carboxylated bead is washed with ethanol and resuspended in ethanol.
2) Glycogen is added to an aqueous sample containing nucleic acid to a concentration of approximately 250 μg/mL (glycogen).
3) This aqueous sample is combined with the bead/ethanol slurry, mixed and incubated for about 15 min. to allow for deposition of nucleic acid on the carboxylated bead.
4) The beads are pelleted by centrifugation or, in the case of paramagnetic beads, concentrated with a magnet.
5) The supernatant is removed and discarded.
6) The bound nucleic acid on the beads is washed three times with a 70% ethanol solution to remove potential impurities, such as residual salts.
7) Bound nucleic acids are recovered by solubilization in a TE elution buffer (10 mM Tris, 1 mM EDTA, pH 8.0).

As may be seen from this exemplary protocol, an inherent advantage to the present invention includes the absence of components that might adversely affect downstream applications following the precipitation of the nucleic acid. In specific embodiments, the precipitation occurs in the absence of potentially undesirable components, such as salt, polyethylene glycol or chaotropic agents. For example, embodiments in which a salt or salts are not included may be particularly desirable in situations in which potential salt carry-over may effect downstream applications.

As disclosed, the precipitation may be carried out in an aqueous solution simply with absolute ethanol, glycogen and the carboxylated substrate. In an alternate embodiment, a salt may be used in the precipitation, such as an acetate salt, chloride salt or ammonium acetate. In embodiments where acetate or chloride salts are used, monovalent salts are preferred.

For removal of nucleic acid from the carboxylated substrate, an elution buffer will generally be used. In general, elution buffer is any aqueous solution in which the salt concentration and ethanol concentration is below the ranges required for binding of DNA onto carboxylated substrate. Standard eluents in accordance with the invention include, for example water and TE. In addition, sucrose (20%) and formamide (100%) solutions can be used to elute the DNA. In general, elution of the DNA from the microparticles occurs in thirty seconds or less when an elution buffer of low ionic strength, for example water, is used. Once the bound DNA has been eluted, the carboxylated substrate may be separated from the elution buffer that contains the eluted DNA, and the substrate may be washed and reused. While temperature does not appear to be critical in the method of separating DNA of the present invention, ambient temperature is preferred. Nevertheless, any temperature above the freezing point of water and below the boiling point of water may be employed in the context of the invention.

As the invention works with both single and double stranded nucleic acids over a broad range, it facilitates the standardization of protocols requiring the isolation, purification, removal or separation of nucleic acid. The disclosed methods and compositions may be carried out rapidly in a single container and are simple to perform, thus allowing for rapid throughput in isolating polynucleotides. Furthermore, the absence of salt in the solution obviates the need for its removal and eliminates potential deleterious effects on downstream applications should significant salt remain. These properties, coupled with its applicability to many procedures useful in molecular biology, make the method amenable to automation.

Particular embodiments of the invention entail the isolation and purification of nucleic acid from cells. In this context, cells are disrupted to form a lysate consisting of the cellular contents. This lysate may be further purified to form a cleared lysate in which the chromosomal DNA, proteins and membranes of the host cells have been selectively removed, such as by chemical treatment or centrifugation, thereby leaving a solution containing plasmid DNA. RNase can be added to create a "cleared lysate" free of RNA, thereby allowing DNA to bind to the magnetic microparticles free from RNA. Methods of creating a cleared lysate are well-known in the art. For example, a cleared lysate can be produced by treating the host cells with sodium hydroxide or its equivalent (0.2N) and sodium dodecyl sulfate (SDS) (1%). This method of creating a cleared lysate is described in detail in Birnboim and Doly, Nucl. Acids Res., 7:1513 (1979); Horowicz and Burke, Nucleic Acids Research 9:2989 (1981), the teachings of which are hereby incorporated herein in their entirety by reference. Similar protocols are well known to similarly isolate lysates comprising, for example: genomic DNA, chromosomal DNA, RNA, mRNA, tRNA, rRNA, viral DNA and RNA, mitochondrial DNA, and/or cloned DNA, such as, for example plasmids bacterial artificial chromosomes (BAC), yeast artificial chromosomes (YAC), cosmids and P1.

As is well known in the art, foreign DNA is introduced into host cells in a variety of molecular biology applications. As reflected above, the disclosed methods and compositions simplify the isolation of cloned DNA from host cells facilitating the production of high quality DNA for sequencing and/or further characterization and processing. In a disclosed embodiment, plasmid DNA recovered after precipitation retains its supercoiled structure indicating that DNA is undamaged in the precipitation process.

The disclosed methods and compositions are also useful for the isolation of single stranded polynucleotides, such as either single stranded DNA or RNA. In a specific embodiment, the present invention facilitates the separation of single stranded polynucleotides from the supernatant of bacterial host cells infected with a recombinant DNA-containing M13 bacteriophage. By way of example, the host cells are removed from the supernatant by filtration (Kristensen, et al., Nucl. Acids Res., 15:550–16 (1987)) or by binding the host cells to amine coated surfaces (Hou and Zaniewski, Biochem, 12:315 (1990). Single stranded DNA is released from the M13 bacteriophage into the solution by adding SDS to a final concentration of between about 0.3% to about 3%, preferably about 1% and at a temperature from about 60° C. to about 100° C., preferably 80° C. Glycogen is added to this lysate, which is then mixed with an appropriate amount of ethanol in the presence of a carboxylated substrate. The substrate is isolated from the solution, washed, and the nucleic acid eluted as further described herein.

In a further embodiment, the nucleic acid containing solution is a solution containing agarose. In such an embodiment, a mixture of nucleic acid is separated, according to methods known to one skilled in the art, such as by electrophoresis on a LMT (Low Melting Temperature) agarose gel. A plug of agarose containing nucleic acid of interest is excised from the gel, placed into a 1.5 mL microcentrifuge tube and cut into small pieces. The tube and gel slice are weighed and the weight of the gel slices determined:

Gel Weight=Weight of slices and tube−Weight of empty tube

The tubes are heated at 70° C. for 10 min. to melt the agarose and then placed at 42° C. for 5 min. to create an agarose solution containing nucleic acid. One unit of Agarase (an agarose digesting enzyme) is added to the tube per 100 mg of agarose and incubated at 42° C. for 30 min. Glycogen is added to this solution, which is then mixed with an appropriate amount of ethanol in the presence of a carboxylated substrate. The substrate is isolated from the solution, washed, and the nucleic acid eluted as further described herein.

In specific embodiments, it is envisioned that some or all of the components necessary for carrying out methods in accordance with the invention may be incorporated into a kit. An exemplary kit comprises reagents necessary to carry out the disclosed methods, such as, for example a carboxylated substrate and a concentrated glycogen solution. An exemplary kit might further include ethanol, suitable wash buffer, elution buffer, reagents for preparing such buffers and/or reagents for isolating nucleic acid from cells, as well as hardware, such as, for example, reaction vessels for carrying out the disclosed methods. It is envisioned that, as the invention can be adapted to high throughput nucleic acid isolation, kits could be specifically designed to facilitate such protocols.

In a still further embodiment, it is envisioned that the methods and compositions disclosed may be incorporated into or performed by an instrument. The instant invention lends itself to automation due to the reliability and relative simplicity of its process and components. It is contemplated that the disclosed compositions and methods could be incorporated into an instrument strictly for the isolation, purification, removal or separation of nucleic acids or an instrument that carries out other manipulation of nucleic acid but that otherwise requires the isolation, purification, removal or separation of nucleic acids in one or more steps. It is contemplated that such an instrument might comprise a means for holding a suitable container such as a reaction vessel. It is further contemplated that such an instrument could be configured to encompass a pipetting means connected to a reservoir capable of dispensing solutions into a reaction vessel. The same or alternate pipetting means could be utilized in removing solutions from the reaction vessel. The pipetting means would be connected to a controller such as a personal computer, such that addition and removal of reagents could be monitored, managed and manipulated.

III. Nucleic Acids

The instant invention concerns methods for manipulating, isolating and purifying a nucleic acid. Basically, a nucleic acid is a polymeric molecule composed of nucleotide subunits. The term "nucleic acid" is well known in the art and as used herein generally refers to a molecule (i.e., a strand)

of DNA, RNA or a derivative or analog thereof, comprising a nucleotide. Nucleotides include, for example, naturally occurring purine or pyrimidine bases found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleotides in length. The term "polynucleotide" refers to at least one molecule of greater than about 100 nucleotides in length.

A nucleic acid may be naturally occurring or may be made by any technique known to one of ordinary skill in the art, such as for example, chemical synthesis or recombinant production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

As used herein a "nitrogenous base" refers to a heterocyclic base, such as for example an adenine, thymine, cytosine, guanine or uracil found in at least one naturally occurring nucleic acid (i.e., DNA and RNA), and naturally or non-naturally occurring derivative(s) as well as analogs of such a nitrogenous base. A nitrogenous base generally can form one or more hydrogen bonds ("anneal" or "hybridize") with at least one other nitrogenous base in manner that may substitute for naturally occurring nitrogenous base pairing (e.g., the hydrogen bonding between A and T, G and C, and A and U).

"Purine" and/or "pyrimidine" nitrogenous base(s) encompass naturally occurring purine and/or pyrimidine nitrogenous bases as well as derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. A table of non-limiting, purine and pyrimidine derivatives and analogs is also provided herein below.

TABLE 1

Purine and Pyrmidine Derivatives or Analogs

| Abbr. | Modified base description | Abbr. | Modified base description |
|---|---|---|---|
| ac4c | 4-acetylcytidine | Mam5s2u | 5-methoxyaminomethyl-2-thiouridine |
| chm5u | 5-(carboxyhydroxylmethyl)uridine | Man q | Beta,D-mannosylqueosine |
| Cm | 2'-O-methylcytidine | McmSs2u | 5-methoxycarbonylmethyl-2-thiouridine |
| cnmm5s2u | 5-carboxymethylaminomethyl-2-thioridine | Mcm5u | 5-methoxycarbonylmethyluridine |
| cmnm5u | 5-carboxymethylaminomethyluridine | Mo5u | 5-methoxyuridine |
| D | Dihydrouridine | Ms2i6a | 2-methylthio-N6-isopentenyladenosine |
| Fm | 2'-O-methylpseudouridine | Ms2t6a | N-((9-beta-D-ribofuranosyl-2-methylthiopurine-6-yl)carbamoyl)threonine |
| gal q | beta,D-galactosylqueosine | Mt6a | N-((9-beta-D-ribofuranosylpurine-6-yl)N-methyl-carbamoyl)threonine |
| Gm | 2'-O-methylguanosine | Mv | Uridine-5-oxyacetic acid methylester |
| I | Inosine | o5u | Uridine-5-oxyacetic acid (v) |
| I6a | N6-isopentenyladenosine | OsYw | Wybutoxosine |
| m 1 a | 1-methyladenosine | P | Pseudouridine |
| m 1 f | 1-methylpseudouridine | Q | Queosine |
| m 1 g | 1-methylguanosine | s2c | 2-thiocytidine |
| m 1 I | 1-methylinosine | s2t | 5-methyl-2-thiouridine |
| m22g | 2,2-dimethylguanosine | s2u | 2-thiouridine |
| m2a | 2-methyladenosine | s4u | 4-thiouridine |
| m2g | 2-methylguanosine | T | 5-methyluridine |
| m3c | 3-methylcytidine | t6a | N-((9-beta-D-ribofuranosylpurine-6-yl)carbamoyl)threonine |
| m5c | 5-methylcytidine | Tm | 2'-O-methyl-5-methyluridine |
| m6a | N6-methyladenosine | Um | 2'-O-methyluridine |
| Mam5u | 5-methylaminomethyluridine | X | 3-(3-amino-3-carboxypropyl)uridine, (acp3)u |

As used herein, a "nucleoside" refers to an individual chemical unit comprising a nitrogenous base linked glycosidically to ribose, deoxyribose, arabinose, or a derivative or an analog of a 5-carbon sugar, but lacking the phosphate residues that would make it a nucleotide. As used herein, a "nucleotide" refers to a nucleoside further comprising a phosphate residue. This phosphate residue is generally the site of covalent attachment between nucleotides to form a nucleic acid.

In general, nucleic acid molecules may comprise single or multiple polymeric strands of nucleotides. A nucleic acid molecule may encompass a double or a triple stranded molecule comprising one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleotides are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891, 625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nitrogenous base, a nitrogenous base linker moeity that is not a 5-carbon sugar, and/or a backbone moiety that is not a phosphate backbone moiety. Examples of nitrogenous base linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

The present invention generally concerns nucleic acid molecules that are isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

The instant invention contemplates the isolation, purification or removal of nucleic acid over a broad size range. As contemplated nucleic acid may be about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges). It will be readily understood that "intermediate lengths" and "intermediate ranges", as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc, about 50,001, about 50,002, etc; about 750,001, about 750,002, etc.; about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc. In certain embodiments, isolation of nucleic acid is of non-native nucleic acid or of an introduced nucleic acid construct, such as, for example, a recombinant vector.

IV. Substrates

The instant invention involves the reversible deposition, association or binding of nucleic acid onto a carboxylated surface. For the purposes of the invention, it is specifically contemplated that a variety of surfaces may be utilized, so long as the surfaces are amenable to being carboxylated. In general, and by way of example, a carboxylated substrate refers to a surface that is coated with or encompasses one or more carboxyl groups or moieties that are capable of reversibly and non-specifically associating with nucleic acid. The carboxyl group acts as a bioaffinity absorbent for DNA in solution. For example, a suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the magnetic microparticle.

Carboxylated substrates may be readily formulated by techniques known to one of skill, see, for example, U.S. Pat. No. 4,695,393 and Cautrecasas, *J. Biol. Chem.*, 245, 3059 (1970). Briefly, an appropriate substrate is silanized with aminophenyl silane. The amino group of the silane is reacted with glutaric anhydride to convert the terminal group from an amine to carboxylic acid by reacting with 0.1 M NaHCO$_3$ followed by the addition of glutaric anhydride. While it is specifically contemplated that one of ordinary skill would be capable of carboxylating appropriate substrates using well known techniques, alternatively, carboxylated substrates are commercially available from a variety of sources, including Dynal, Inc. and Seradyn.

A. Microparticles and Beads

Microparticles useful in the present invention may be a variety of shapes, which can be regular or irregular; preferably the shape maximizes the surface areas of the microparticles. Microparticles should be of such a size that their separation from solution, for example by centrifugation, filtration or magnetic separation, is not difficult. In addition, microparticles should not be so large that surface area is minimized or that they are not suitable for microscale operations. Suitable sizes range from about 0.1 μm mean diameter to about 100 μm mean diameter. A preferred size is about 1.0 μm. mean diameter. Exemplary microparticles useful in the context of the invention are commercially available from Seradyn [Ramsey, Minn.] (Sera-Mag™ Magnetic Carboxylate-Modified microparticles (MG-CM), Catalog number 44152105050250).

1. Paramagnetic Microparticles

A skilled artisan recognizes that there are multiple means in the art to prepare magnetic particles, such as are described in U.S. Pat. No. 4,774,265 and U.S. Pat. No. 4,695,393. Magnetic microparticles are attracted by a magnetic field, which facilitates concentration and purification of compounds bound to the microparticles. Exemplary magnetic microparticles useful in the compositions and methods of the present invention may, for example, comprise a magnetic metal oxide core, surrounded by an adsorptively or covalently bound silane coat to which one or more carboxyl groups are covalently bound through selected coupling chemistries, thereby coating the surface of the microparticles with functional groups. The magnetic metal oxide core is often iron oxide, with iron as a mixture of $Fe^{2+}$ and $Fe^{3+}$. A standard $Fe^{2+}/Fe^{3+}$ ratio is 2/1, but can vary from about 0.5/1 to about 4/1.

Suitable amino silanes useful to coat the microparticle surfaces include p-aminopropyltrimethoxysilane, N-2-aminoethyl-3-aminopropyltrimethoxysilane, triamino-functional silane ($H_2NCH_2$—NH—$CH_2CH_2$—NH—$CH_2$—Si—$(OCH_3)_3$, n-dodecyltriethoxysilane and n-hexyltrimethoxysilane. Methods of preparing these microparticles are described in U.S. Pat. Nos. 4,628,037, 4,554,088, 4,672,040, 4,695,393 and 4,698,302, the teachings of which are hereby incorporated by reference into this application in their entirety. These patents disclose other amino silanes which are suitable to coat the iron oxide core and which are encompassed by this invention. Magnetic microparticles comprising an iron oxide core, as described above, without a silane coat may also be used in the method of the present invention if they are capable of being modified to include carboxyl groups. Polymer encapsulated microparticles are commercially available from a variety of sources (i.e. Dynal, Inc., Dynabeads M-270 (Cat. No. 143.05)) and are generally preferred. The advantage of having an encapsulated metal oxide core is illustrated by the observation that washing the magnetic microparticles with EDTA removes some of the iron and reduces the ability of the magnetic microparticles to bind DNA.

2. Alternate Bead Substrates

A variety of materials that may be carboxylated may also be formulated as beads. In the context of the instant invention it is contemplated that carboxylated beads may take the form of materials known to one of skill that may be carboxylated, such as for example polystyrene, polypropylene, nylon, glass, polyethylene, polycarbonate, silicon, agarose, and acrylamide. It is expressly contemplated that beads may be used for both column and/or batch preparations. One of ordinary skill would thus be aware of techniques of utilizing carboxylated beads in a column or added to an aqueous solution for batch separation.

B. Reaction Vessels

It is specifically contemplated that the methods and compositions of the invention may be used in conjunction with reaction vessels specifically modified such that surfaces encompass carboxyl groups. Thus, test tubes, microcentrifuge tubes, multi-well plates, petri dishes, conical tubes and other reaction vessels may be specifically modified to encompass carboxyl groups on surfaces. In a specific embodiment, the interior of a polystyrene tube is coated with carboxyl groups. In this embodiment, the aqueous nucleic acid sample, ethanol and glycogen are added directly to the tube, mixed, and incubated on ice for approximately 15 minutes. The liquid is then removed, the tube washed with 70% ethanol, and the nucleic acid eluted with water or TE. It is envisioned that the methods and compositions of the instant invention will be equally applicable to other reaction vessels that can be likewise modified with carboxyl groups. Suitable reaction vessel materials are well known in the art, but may include, for example, polystyrene, polypropylene, nylon, glass, polyethylene, polycarbonate and silicon.

C. Membranes

It is specifically contemplated that the methods and compositions of the invention may be used in conjunction with membranes modified such that surfaces encompass carboxyl groups. One of ordinary skill would be aware of a variety of membrane materials that could be carboxylated, examples of which include: nylon, nitrocellulose, nylon-reinforced nitrocellulose, acetate, PTFE, polycarbonate, glass, cellulose acetate, polyester, polyethersulfone (PES), polysulfone, PVDF, and DEAE.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

General Precipitation Protocol:

For each of the given examples, carboxylated magnetic beads were prepared and precipitations carried out as described below:

1. 700 µL 100% ETOH was placed into a low adhesion microcentrifuge tube.
2. The bottle containing the magnetic beads [Seradyn (Ramsey, Minn.) Sera-Mag™ Magnetic Carboxylate-Modified microparticles (MG-CM), Catalog number 44152105050250] was swirled until the beads were completely suspended.
3. 70 µL beads were pipetted into the tube with ETOH and mixed by inversion. The tube was centrifuged briefly and placed into a magnet holder.
4. The supernatant was discarded and the tube was immediately removed from the magnet and placed in a holder on the benchtop. 700 µL 100% ETOH was added and the tube inverted until a suspension was formed and then centrifuged briefly.
5. The tube was returned to the magnet and the supernatant removed. This wash step was repeated twice as above.
6. After the last wash, the beads were resuspended in 700 µL 100% ETOH and placed on ice.
7. The volume of nucleic acid to be precipitated was brought to 200 µL with TE (10 mM Tris, 1 mM EDTA, pH 8.0). 3 µL 20 mg/mL glycogen (MBI Fermentas) only, or 3 µL 20 mg/mL glycogen and 100 µL 10M Ammonium Acetate were added to the nucleic acid solution. The nucleic acid solution was mixed well by inversion and then centrifuged briefly.
8. The nucleic acid solution was added to the washed beads and mixed by inverting the tube. The tube was then centrifuged briefly.
9. The nucleic acid/bead slurry was placed on ice for 15 min.
10. The nucleic acid/bead slurry was then returned to the magnet and the supernatant removed.
11. 700 µL 70% ETOH was added to the tube and mixed by inversion. The tube was centrifuged briefly and then returned to the magnet. The supernatant was removed and the wash repeated twice. On the last wash, as much remaining supernatant as possible was removed from the tube. The tube was then centrifuged and returned to the magnet. Residual 70% ETOH was carefully removed.

12. The beads were dried for 2–5 min. at room temperature. Drying was carefully monitored to prevent the bead pellet from cracking or caking in the tube.
13. The beads were resuspended in an appropriate amount of TE or water and vortexed to mix. The suspension was then placed at room temperature for 10 min.
14. The tube was returned to the magnet and the supernatant containing the nucleic acid recovered.

Example 1

Plasmid DNA recovery from solution:

1. 100 ng, 250 ng, 500 ng, 1 µg, 10 µg and 50 µg of plasmid DNA (pBSTK-Stratagene) were added to a final volume of 200 µL TE (10 mM Tris, 1 mM EDTA, pH 8.0) in microcentrifuge tubes.
2. 100 µL 10M ammonium acetate and 3 µL 20 mg/mL glycogen (MBI Fermentas) were added to the DNA and mixed.
3. The DNA mixture was added to carboxylated magnetic beads and the precipitation carried out as described. DNA was recovered in 20 µL to 1 mL TE.
4. Assuming 100% recovery, aliquots of recovered DNA (estimated amounts 100 ng or 500 ng) were electrophoresed (70V) on a 1% agarose gel containing 0.5 µg/mL ethidium bromide, alongside 100–500 ng of non-precipitated plasmid. Gels were visualized using a fluorimager (Syngene).
5. Bands from precipitated samples were compared to non-precipitated controls by densitometry. These values were then used to calculate the amount of DNA in bands from precipitated samples and a percent recovery calculated.

Figure 1:
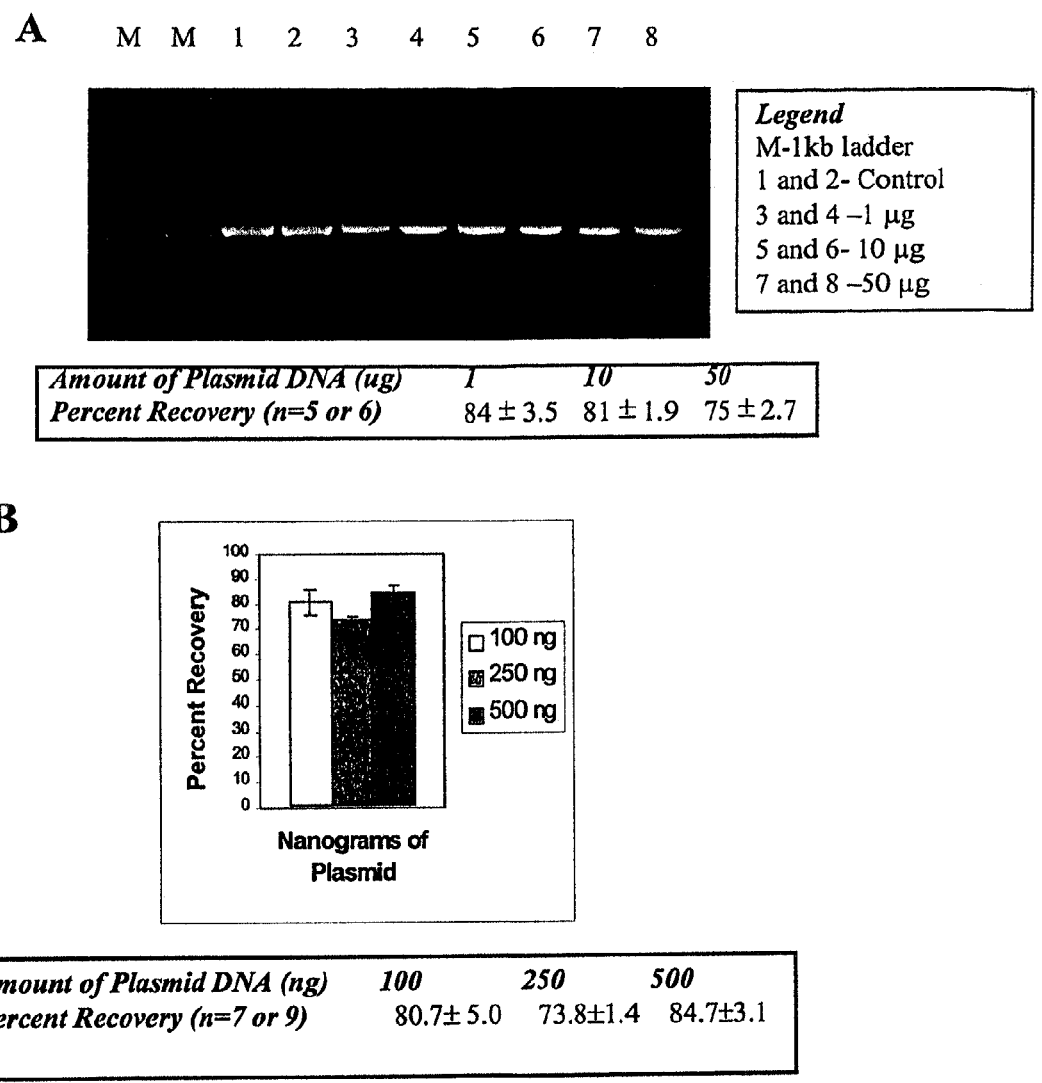
FIG. 1 Plasmid DNA recovery from solution. Differing amounts of plasmid DNA (pBSTK-Stratagene) were precipitated onto carboxylated magnetic beads. An aliquot of recovered DNA was visualized next to a non-precipitated control on a 1% agarose gel containing 0.5 µg/mL ethidium bromide, using a Fluorimager.
Figure 2:
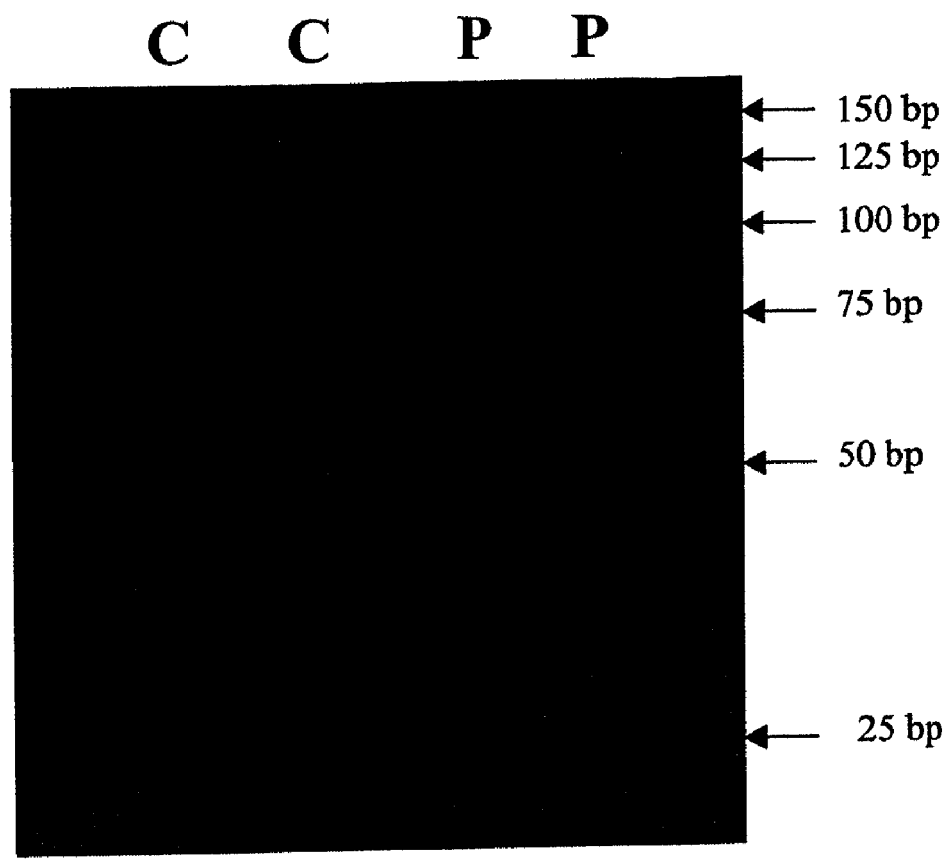
Figure 3:
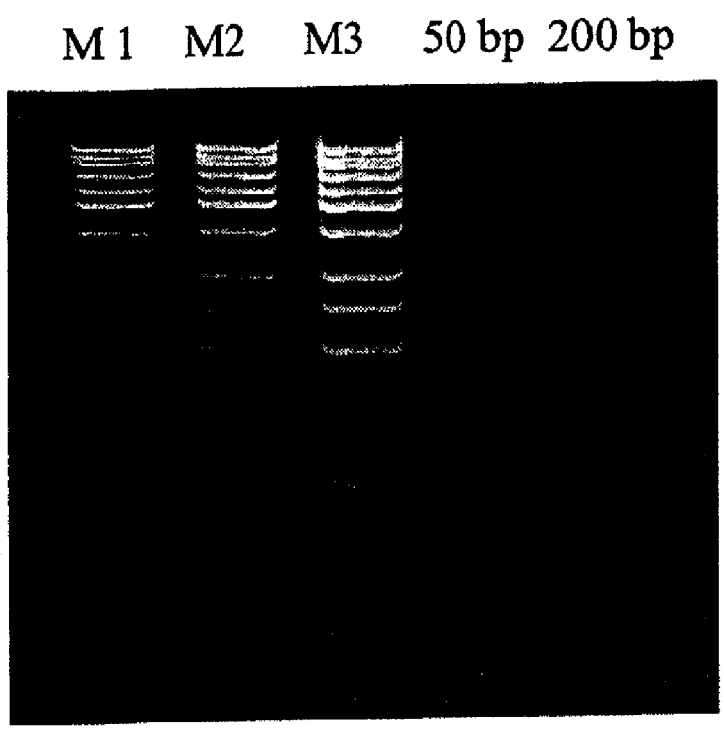
Figure 4:
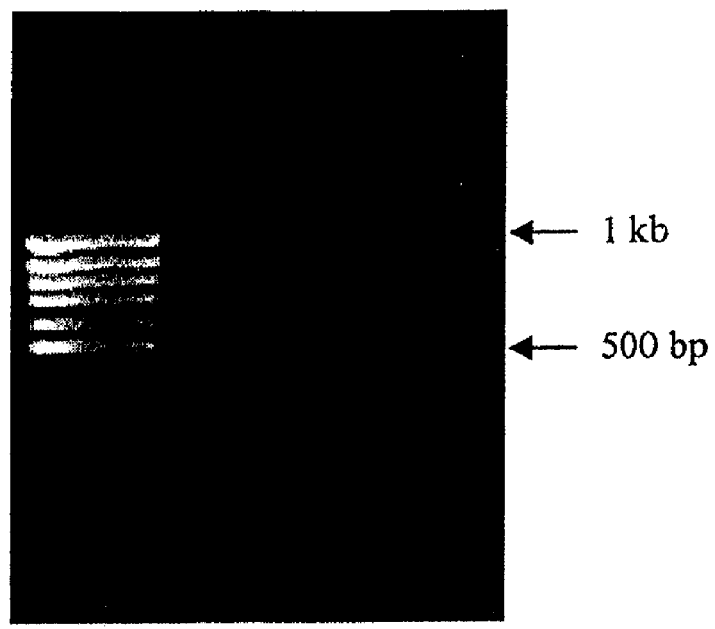
Figure 5:
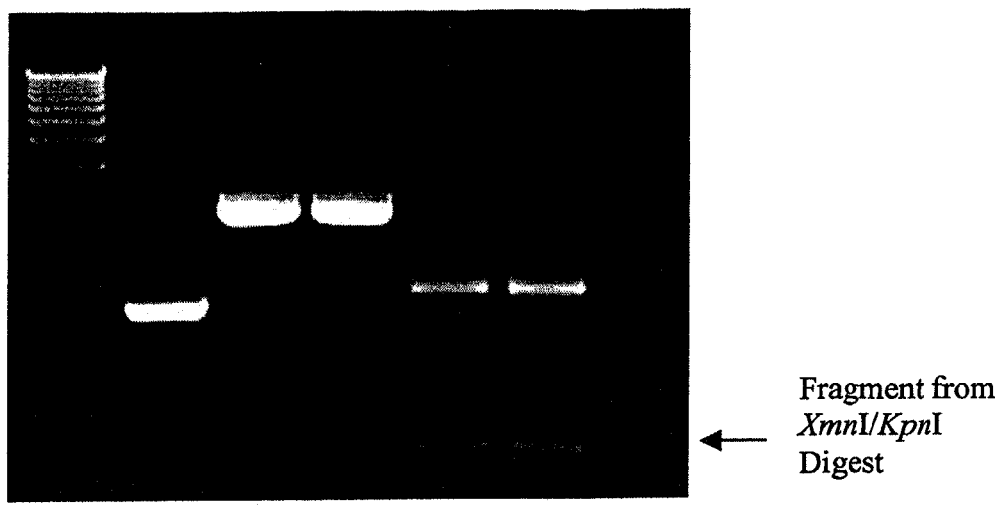

Precipitation of up to 50 µg of plasmid DNA yielded recoveries of 80% (FIG. 1A). Nanogram quantities of plasmid (100, 250 and 500 ng) were recovered in at least the 75% range (FIG. 1B). Comparable results were seen using salt-free conditions. Additionally, plasmid DNA recovered after precipitation retained its supercoiled structure indicating that DNA was undamaged in the precipitation process.

Example 2

Recovery of small fragments from solution:

1. 1 µg (2.9 µL) of a DNA ladder (25 bp ladder, Promega) was added to a final volume of 200 µL TE (10 mM Tris, 1 mM EDTA, pH 8.0) in microcentrifuge tubes.
2. 100 µL 10M ammonium acetate and 3 µL 20 mg/mL glycogen (MBI Fermentas) were added to the DNA and mixed by vortexing.
3. The DNA mixture was then added to carboxylated magnetic beads and the precipitation carried out as described. DNA was recovered in 25 µL TE.
4. Assuming 100% recovery, aliquots of recovered DNA estimated to be 200 ng were electrophoresed (150V) on an 8% polyacrylamide gel alongside 200 ng of non-precipitated ladder.
5. Gels were stained with SYBR® Green 1 [BMA] (1/10,000 dilution in 1×TBE) and visualized using a Fluorimager.
6. Bands from precipitated samples were compared to non-precipitated controls by densitometry. These values were then used to calculate the amount of DNA in bands from precipitated samples and a percent recovery calculated.

Compared to the non-precipitated control, 75% of the 25 bp fragment was recovered, while recoveries of the 50, 75, 100, 125 and 150 bp fragments were in the 90% range.

Example 3

Recovery of small double stranded DNA fragments from polyacrylamide gels:

1. 8 µL and 14 µL of the GeneRuler™ 50 bp quantitation ladder (MBI Fermentas) were electrophoresed on an 8% polyacrylamide gel.
2. The 50 bp fragment corresponding to 196 ng was excised from the lane containing 14 µL of the ladder.
3. The 200 bp fragment corresponding to 228 ng was excised from the lane containing 8 µL of the ladder.
4. The fragments were placed into separate 1.5 mL microcentrifuge tubes and crushed into fine pieces with a pipette tip.
5. 300 µL of Binding Buffer (3.3 M ammonium acetate in TE [10 mM Tris, 1 mM EDTA, pH 8.0]), or, for salt-free conditions (TE only), were added to the crushed gel slices.
6. The tubes were incubated at 65° C. for 4 h with occasional mixing.
7. The tubes were cooled on ice and centrifuged for 5 min. at 14,000×g in a microcentrifuge.
8. The supernatant containing the eluted DNA was carefully removed and placed into a new 1.5 mL microcentrifuge tube. 3 µL glycogen (20 mg/mL, MBI Fermentas) was added.
9. The mixture was then combined with carboxylated magnetic beads and precipitated as described.
10. The DNA was eluted from the beads in 20 µL TE.
11. 4 µL aliquots were electrophoresed on an 8% polyacrylamide gel next to 0.25 µL, 0.5 µL and 1 µL of the quantitation ladder.
12. Gels were stained with SYBR® Green 1 [BMA] (1/10,000 dilution in 1×TBE) and visualized using a fluorimager. Recovery was assessed using densitometry by comparing bands from recovered DNA to bands of equivalent intensity on the quantitation ladder. These values were used to calculate a percent recovery.

Recoveries were typically in the 50% range, using only 50–200 ng of starting material. Yields can approach 80%. Comparable results were obtained under salt-free conditions.

Example 4

Recovery of fragments from agarose gels:

1. 4 µL of the GeneRuler™ 50 bp Quantitation ladder from MBI Fermentas was electrophoresed on a 1% LMT agarose (SeaPlaque® GTG® agarose, BMA) gel at 75 V.
2. Bands corresponding to 500 bp (284 ng) and 1 kb (292 ng) were excised, placed into separate 1.5 mL microcentrifuge tubes and cut into small pieces.
3. The tubes and gel slices were weighed, and the weight of the slices was determined:
4. Gel Weight=Weight of slices and tube−Weight of empty tube
5. The tubes were heated at 70° C. for 10 min. to melt the agarose and then placed at 42° C. for 5 min.
6. One unit of Agarase (MBI Fermentas) was added to each tube/100 mg of agarose, and incubation was continued at 42° C. for 30 min. The volume of the sample was then adjusted as necessary to 200 μL with TE.
7. 100 μL 10 M ammonium acetate and 3 μL 20 mg/mL glycogen (MBI Fermentas) were added to the tube. For precipitation under salt free conditions, the ammonium acetate was omitted.
8. The DNA solution was added to washed beads and precipitated as described. DNA was recovered in 20 μL TE (10 mM Tris, 1 mM EDTA, pH 8.0).
9. 2 μL aliquots of recovered material were electrophoresed (70V) on a 1% agarose gel containing 0.5 μg/mL ethidium bromide. 1 μL of the quantitation ladder was loaded.
10. Gels were visualized using a fluorimager. Recovery was assessed using densitometry by comparing bands from recovered DNA to bands of equivalent intensity on the quantitation ladder. These values were used to calculate a percent recovery.

Recoveries were typically in the 80% range, starting from approximately 300 ng of DNA. Under salt-free conditions, recoveries were comparable.

Example 5

Use of carboxylated beads for buffer exchange:
1. 5 μg of pBSTK (Stratagene) was digested with 20 units of XmnI restriction enzyme (Invitrogen) in a final volume of 20 μL in 1×Restriction Enzyme Buffer at 37° C. for 1 h.
2. The digested material was precipitated onto carboxylated magnetic beads as described and recovered in 10 μL TE (10 mM Tris, 1 mM EDTA, pH 8.0).
3. An aliquot (approximately 1 μg) of digested plasmid was further incubated with 20 units of KpnI enzyme (Invitrogen) in a final volume of 40 μL in 1×KpnI Restriction Enzyme Buffer at 37° C. for 1 h.
4. XmnI digested and XmnI/KpnI digested samples were electrophoresed (70V) on a 1% agarose gel containing 0.5 μg/mL ethidium bromide. Gels were visualized using a fluorimager.

The fragment released from the plasmid by the double digest was easily detected. This indicated that carboxylated beads can replace phenol/chloroform in buffer/enzyme exchange protocols.

Example 6

Use of carboxylated beads for cDNA clean-up and RAG-Etag preparation:

A) cDNA Cleanup
1. 10 μg of total RNA from the human breast cancer cell line (MCF-7) was used to synthesize cDNA with the SuperScript Choice System (Invitrogen) and Biotinylated Oligo dT from the RAGEtag Synthesis Kit (KPL) as follows. All reactions were carried out in low adhesion microcentrifuge tubes (ISC BioExpress).

| Component | Volume |
|---|---|
| RNA (10 μg) | var |
| 10 mM dNTP mix | 2.5 μl |
| Biotinylated Oligo dT | 6.5 μL |
| DEPC-treated Water | var |
| Final Volume | 32.5 μL |

2. The mixture was incubated at 70° C. for 5 min. and chilled on ice.
3. The following components were added on ice:

| Component | Volume |
|---|---|
| 5X First Strand Buffer | 10 μL |
| 0.1 M DTT | 5 μL |
| Superscript II | 2.5 μL |
| Final Volume | 17.5 μL |

4. The tube was mixed and incubated at 37° C. for 1 h.
5. The tube was placed on ice and the following components added:

| Component | Volume |
|---|---|
| DEPC-treated Water | 289.5 μL |
| 10 mM dNTP mix | 7.5 μL |
| 10X Second Strand Buffer | 40 μL |
| DNA Polymerase I | 10 μL |
| RNAse H | 1.75 μL |
| DNA Ligase | 1.25 μL |
| Final Volume | 400 μL |

6. The tube was mixed and incubated at 16° C. for 2–4 h.
7. 5 μL of RNaseA/T1(Ambion) was added and the tube incubated at 37° C. for 30 min.
8. The sample was precipitated as described with the following modifications: 6 μL of glycogen and 200 μL of 10 M ammonium acetate were added. The DNA mixture was then combined with carboxylated magnetic beads for precipitation.
9. The cDNA was recovered in 20 μL TE (10 mM Tris, 1 mM EDTA, pH 8.0) and quantitated using a spectrophotometer.
10. One ng of cDNA was then used to analyze cDNA quality using KPL's cDNA Integrity kit:

| Component | Final Volume |
|---|---|
| cDNA (1 ng) | variable |
| 5X PCR Buffer | 5 μL |
| Taq DNA Polymerase (5 u/μL) | 0.25 μL |
| 5' or 3' Primer Set (clathrin, GAPDH, Actin or ARF-F1) | 1 μL |
| Final Volume | 25 μL |

| PCR conditions: | | |
|---|---|---|
| 94° C. | 2 min. | 1 cycle |
| 94° C. | 30 sec. | |
| 55° C. | 1 min. | 25 cycles |
| 72° C. | 30 sec. | |
| 72° C. | 7 min. | 1 cycle |
| Hold | 4° C. | |

11. 5 μL of PCR reactions were visualized on an 8% polyacrylamide gel. Gels were stained with SYBR® Green 1 [BMA] (1/10,000 dilution in 1×TBE) and visualized using a Fluorimager.

B) RAGEtag preparation for GS320™ analysis using carboxylated magnetic beads. One and a half μg of cDNA was used to prepare RAGEtags from four different cDNA samples (H1, H2 H3 and H4) using KPL's RAGEtag Synthesis Kit. cDNA was first bound to streptavidin coated magnetic beads and then sequentially digested with a total of two restriction enzymes. Universal A and B linkers were then ligated, and sequentially digested DNA fragments containing both A and B linkers were recovered. Specific genes were amplified by selecting the appropriate primer pair from a combinatorial library of 320 primers. RAGEtags were prepared from cDNA (previously cleaned up by precipitation onto carboxylated magnetic beads) as follows:

1. 1.5 µtg cDNA was combined with 70 µL 2× Binding Buffer and water to a final volume of 140 µL. This mixture was combined with 100 µL streptavidin-coated magnetic beads which were washed thrice in 1× Binding Buffer.
2. The mixture was incubated at room temperature for 30 min.
3. The beads were immobilized on a magnet and the supernatant removed. The beads were then washed 3 times with 200 µL of 1×DpnII buffer and resuspended in a final volume of 95 µL 1×DpnII Buffer.
4. 5 µL of DpnII was added, and the tube was incubated at 37° C. for 1 h.
5. The beads were immobilized on a magnet and the supernatant removed.
6. The beads were washed thrice with 200 µL of 1×Hsp92II Buffer and resuspended in a final volume of 93 µL 1×Hsp92II Buffer.
7. 5 µL of Hsp92II and 2 µL of 100×BSA were added. The tube was mixed and incubated at 37° C. for 1 h.
8. The beads were immobilized on a magnet and the supernatant recovered.
9. 100 µL TE (10 mM Tris, 1 mM EDTA, pH 8.0),100 µL, 10 M ammonium acetate and 3 µL 20 mg/mL glycogen (MBI Fermentas) were added and the DNA mixture combined with carboxylated magnetic beads as described. (10 M ammonium acetate may be omitted from this step).
10. The DNA was recovered in 25 µL TE.
11. 5 µL 10× Ligase Buffer, 5 µL Biotinylated Linker B and 5 µL Linker A were added.
12. The tube was mixed and incubated at 50° C. for 2 min. and placed at room temperature for 15 min.
13. 2 µL DNA Ligase was added and the incubation continued at room temperature for up to 1 h.
14. 100 µL 2× Binding Buffer and 50 µL water was added to the ligation. This mixture was added to streptavidin-coated magnetic beads which were prepared as in step 1.
15. The mixture was incubated at room temperature for 30 min.
16. The beads were immobilized on a magnet and the supernatant removed.
17. The beads were washed thrice in TE, and then resuspended in a final volume of 100 µL TE.
18. The samples were subjected to GS320™ analysis as described (U.S. Pat. No. 6,221,600, Wang et al., Nucleic Acids Res. Dec. 1, 1999; 27(23): 4609–4618).
19. 5 µL of the PCR reactions were visualized on 8% polyacrylamide gels. Gels were stained with SYBR® Green 1 [BMA] (1/10,000 dilution in 1×TBE) and visualized using a fluorimager.

Figure 6:
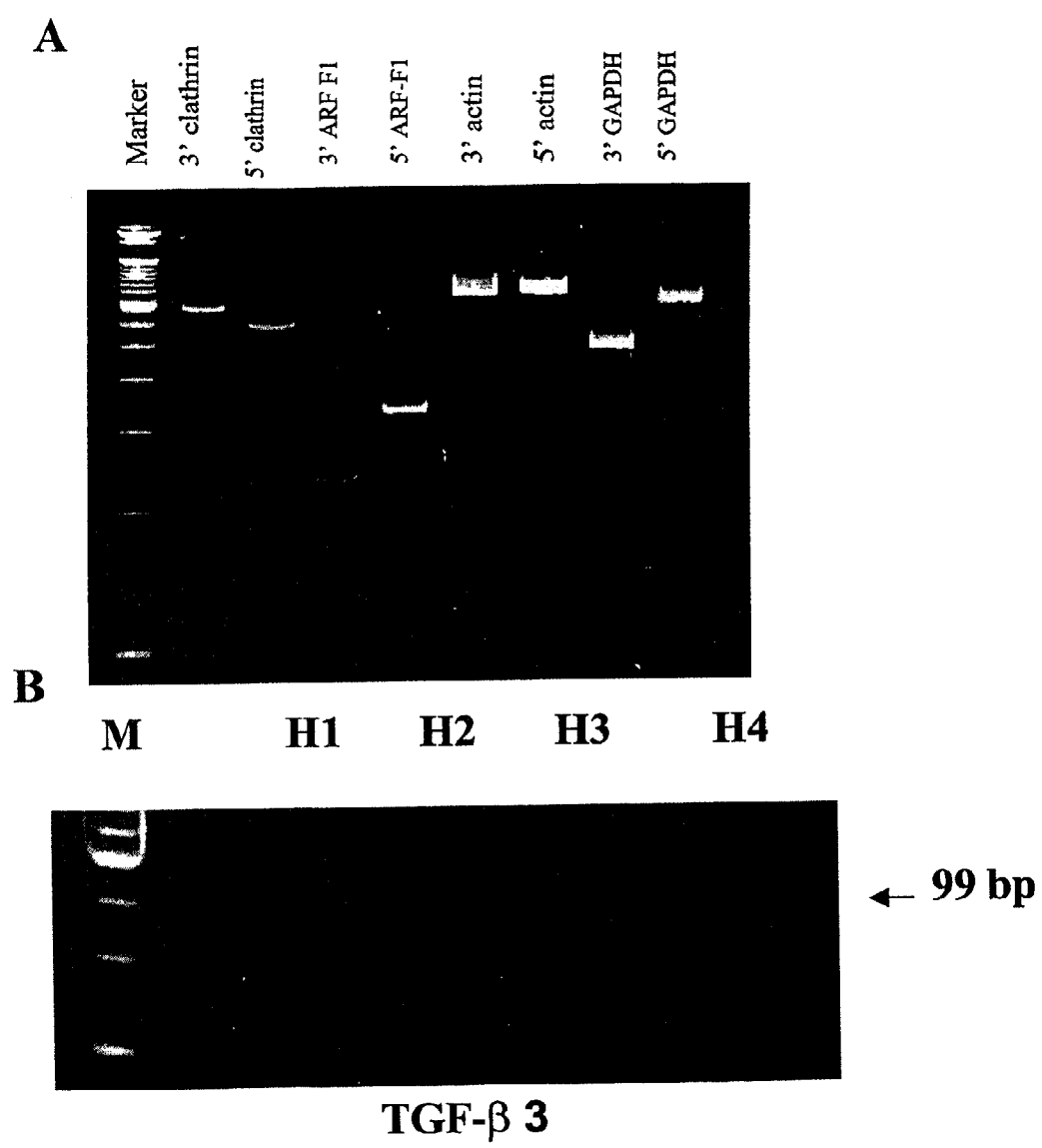
Figure 7:
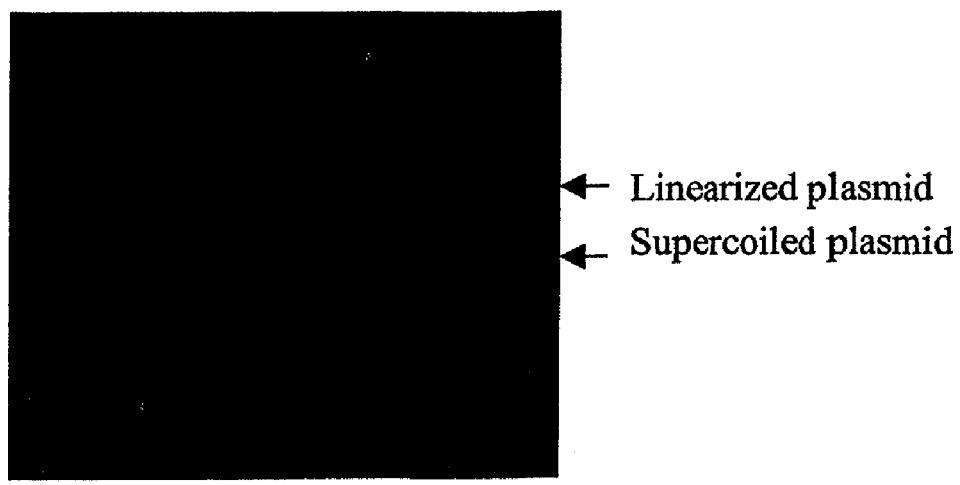
Figure 8:
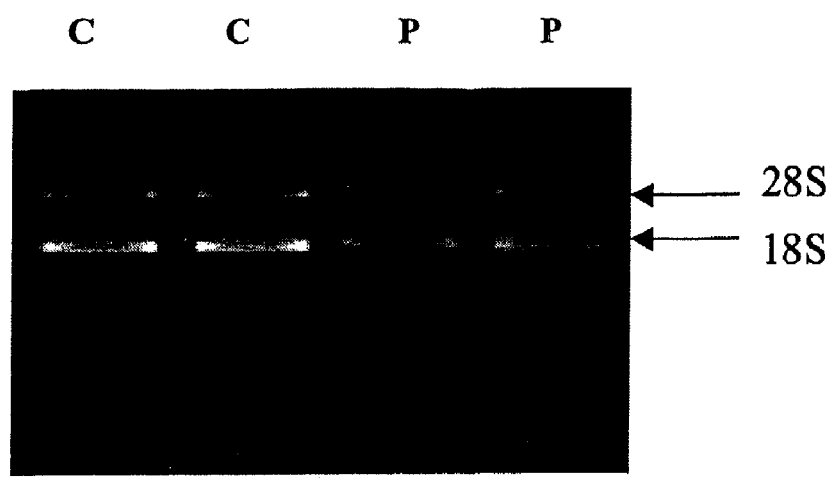

The presence of 5' and 3' end fragments of common housekeeping genes, amplified using the primer pairs provided in the kit, indicated full-length, high quality cDNA (FIG. 6A). cDNA purified using this method has been used successfully in GS320™ analysis repeatedly (FIG. 6B). RAGEtag preparations which incorporate the carboxylated magnetic beads have also been used repeatedly for GS320™ analysis. The data indicate that TGF-β is downregulated in H1, H2 and H4, compared to H3.

Example 7

Recovery of Plasmid DNA from a cleared lysate:
1. A single bacterial colony of Bluescript plasmid in DH5α cells (Invitrogen) was inoculated into 1.5 mL of Luria Broth with 100 µg/mL ampicillin.
2. After growth overnight at 37° C. with shaking, plasmid DNA was isolated by the alkaline lysis method using solutions from Bio-Rad's Quantum® Prep Plasmid Maxiprep Kit with modified volumes as follows.
3. The overnight culture was spun at 14,000×g in a microcentrifuge at 4° C. for 10 min. The supernatant was discarded.
4. 100 µL of Cell Resuspension Solution (with RNAse A) was added to the pellet and resuspended by pipetting up and down.
5. 150 µL Cell Lysis Solution was added and the tube was gently mixed by inverting several times. After mixing incubation was done at room temperature for 5 min.
6. 100 µL Neutralization Solution was added and the tube mixed by inversion. The tube was immediately transferred to a microcentrifuge at 4° C. and centrifuged at 14,000×g for 10 min.
7. The cleared lysate was recovered and placed into a clean microcentrifuge tube.
8. 3 µL glycogen (20 mg/mL-MBI Fermentas) was added and the DNA precipitated onto carboxylated magnetic beads as described.
9. The DNA was recovered in 25 µL TE (10 mM Tris, 1 mM EDTA, pH 8.0).
10. For complete removal of RNA, an RNase treatment step was added. The entire sample was incubated with 10 µg (1 µL 10 mg/mL stock) RNaseA (Sigma) for 30 min. at room temperature.
11. 5 µL of the plasmid miniprep was digested with 20 units of EcoRI enzyme (Invitrogen) in 1×EcoRI Buffer at 37° C. for 1 h.
12. 5 µL of uncut plasmid and 5 µL of the digested sample were resolved on a 1% agarose gel containing 0.5 µg/mL ethidium bromide. Gels were visualized using a Fluorimager.

Supercoiled plasmid DNA was recovered and successfully linearized by EcoRI. Yields of plasmid DNA approached 3 µg.

Example 8

Recovery of Total RNA using carboxylated beads:
1. 5 µg of total Mouse Liver RNA (Origene) was brought to 200 µL with DEPC-treated water.
2. 100 µL 10 M ammonium acetate and 3 µL 20 mg/mL glycogen (MBI Fermentas) was added and the solution mixed.
3. The RNA mixture was added to carboxylated magnetic beads and precipitated as described.
4. The RNA was recovered in 50 µL DEPC-treated water.
5. Assuming 100% recovery, an aliquot of recovered RNA estimated to be 1 µg was mixed with 2× volume of RNA Loading Solution (Sigma) containing ethidium bromide. 1 µg of unprecipitated RNA was also combined with 2× volume RNA Loading Solution. The RNA samples were heated at 68° C. for 10 min then cooled on ice prior to loading.

6. RNA was electrophoresed on a 1% agarose/formaldehyde gel at 60V. Visualization was done using a Fluorimager.
7. Recovery was assessed using densitometry by comparing bands from recovered RNA to bands from unprecipitated RNA. These values were used to calculate a percent recovery.

RNA was recovered intact and percent recovery was in the 60% range.

Example 9

DNA precipitation with acetate salts:
1. 1 μg (2.9 μL) of a DNA ladder (25 bp ladder, Promega) was added to 1.5 mL microcentrifuge tubes containing a final concentration of 3.3 M salt in a volume of 300 μL. Salts were either ammonium acetate, potassium acetate, sodium acetate or magnesium acetate.
2. 3 μL of 20 mg/mL glycogen (MBI Fermentas) was added to the DNA and mixed.
3. The DNA mixture was combined with carboxylated magnetic beads and the precipitation carried out as described. DNA was recovered in 25 μL TE (10 mM Tris, 1 mM EDTA, pH 8.0).
4. Assuming 100% recovery, aliquots of recovered DNA estimated to be 200 ng were electrophoresed (150V) on an 8% polyacrylamide gel alongside 200 ng of non-precipitated ladder.
5. Gels were stained with SYBR® Green 1 [BMA] (1/10,000 dilution in 1×TBE) and visualized using a Fluorimager.

Several commonly used monovalent acetate salts support DNA precipitation onto carboxylated beads. However magnesium acetate, which is a divalent salt, does not.

Example 10

DNA precipitation with chloride salts:
1. 1 μg (2.9 μL) of a DNA ladder (25 bp ladder, Promega,) was added to 1.5 mL microcentrifuge tubes containing a final concentration of 3.3 M salt in a volume of 300 μL. Salts were either sodium chloride, lithium chloride, magnesium chloride, potassium chloride or ammonium acetate (included for comparison).
2. 3 μL of 20 mg/mL glycogen (MBI Fermentas) was added to the DNA and mixed.
3. The DNA mixture was then added to carboxylated magnetic beads and the precipitation carried out as described. DNA was recovered in 25 μL TE (10 mM Tris, 1 mM EDTA, pH 8.0).
4. Assuming 100% recovery, aliquots of recovered DNA estimated to be 200 ng were electrophoresed (150V) on an 8% polyacrylamide gel alongside 200 ng of non-precipitated ladder.
5. Gels were stained with SYBR® Green 1 [BMA] (1/10,000 dilution in 1×TBE) and visualized using a Fluorimager.

Sodium and lithium chloride salts supported DNA precipitation onto carboxylated magnetic beads. However, both potassium and magnesium chloride salts were less efficient compared to ammonium acetate. Potassium chloride also led to clumping of the carboxylated beads.

Example 11

Glycogen titration:
1. 1 μg (2.9 μL) of DNA ladder (25 bp ladder, Promega,) was added to 1.5 mL microcentrifuge tubes containing a final volume of 200 μL TE (10 mM Tris, 1 mM EDTA, pH 8.0).
2. Either 2 μg (1 μL of a 1/10 dilution of the stock 20 mg/mL), 20 μg (1 μof stock 20 mg/mL), 60 μg (3 μL of stock 20 mg/mL) or 120 μg (6 μL of stock 20 mg/mL) glycogen (MBI Fermentas) was added to the DNA and mixed.
3. The DNA mixture was combined with carboxylated magnetic beads and the precipitation carried out as described. DNA was recovered in 25 μL TE.
4. Assuming 100% recovery, aliquots of recovered DNA estimated to be 200 ng were electrophoresed (150V) on an 8% polyacrylamide gel alongside 200 ng of non-precipitated ladder.
5. Gels were stained with SYBR® Green 1 [BMA] (1/10,000 dilution in 1×TBE) and visualized using a Fluorimager.
6. Bands from precipitated samples were compared to non-precipitated controls by densitometry. These values were then used to calculate the amount of DNA in bands from precipitated samples and a percent recovery calculated.

A range of glycogen concentrations was effective for precipitation of DNA. Concentrations ranging from 100 μg/mL to 600 μg/mL resulted in at least 80% percent recoveries for 25 bp–1.8 kb fragments using 1 μg of a DNA ladder.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

One skilled in the art readily appreciates that the patent invention is well adapted to carry out the objectives and obtain the ends and advantages mentioned as well as those inherent therein. Methods, compositions, kits, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PATENTS

U.S. Pat. No. 5,898,071
U.S. Pat. No. 6,310,199
U.S. Pat. No. 5,705,629
U.S. Pat. No. 4,683,202
U.S. Pat. No. 4,682,195
U.S. Pat. No. 5,645,897
U.S. Pat. No. 5,908,845
U.S. Pat. No. 5,786,461
U.S. Pat. No. 5,891,625,
U.S. Pat. No. 5,773,571
U.S. Pat. No. 5,766,855
U.S. Pat. No. 5,736,336
U.S. Pat. No. 5,719,262
U.S. Pat. No. 5,714,331
U.S. Pat. No. 5,539,082
U.S. Pat. No. 4,695,393
U.S. Pat. No. 4,774,265
U.S. Pat. No. 4,695,393.
U.S. Pat. No. 4,628,037
U.S. Pat. No. 4,554,088
U.S. Pat. No. 4,672,040
U.S. Pat. No. 4,695,393
U.S. Pat. No. 4,698,302
U.S. Pat. No. 6,221,600
WO 92/20702

PUBLICATIONS

Birnboim, et al., Nucleic Acids Res. Nov. 24, 1979;7(6): 1513–23.
Birnboim, Methods Enzymol. 1983;100:243–55.
Brisco et al., Promega Notes 2001; 79: 18–21.
Cautrecasas, J. Biol. Chem., 245, 3059 (1970)
DeAngelis, et al. Nucleic Acids Res. Nov. 25, 1995;23(22): 4742–3.
Eickbush, et al., Cell. 13(2):295–306 (1978).
Horowicz and Burke, Nucleic Acids Research 9:2989 (1981)
Wang et al., Nucleic Acids Res. 27(23): 4609–4618, (1999).

We claim:

1. A method of isolating nucleic acid, comprising:
   contacting a composition comprising nucleic acid with an effective amount of glycogen to facilitate precipitation of nucleic acid and ethanol in the presence of a carboxylated paramagnetic bead, wherein said contact results in the association of the nucleic acid with the carboxylated paramagnetic bead and further wherein the precipitation occurs in the substantial absence of salt.

2. The method of claim 1, wherein said nucleic acid is subsequently eluted from the paramagnetic bead.

3. The method of claim 1, wherein an effective amount of glycogen comprises from about 1 µg/ml to about 1000 µg/ml.

4. The method of claim 3, wherein an effective amount of glycogen comprises from about 200 µg/ml to about 500 µg/ml.

5. The method of claim 4, wherein an effective amount of glycogen comprises about 250 µg/ml.

6. The method of claim 1, wherein said nucleic acid is DNA.

7. The method of claim 6, wherein the DNA is genomic DNA.

8. The method of claim 6, wherein the DNA is plasmid DNA.

9. The method of claim 6, wherein the DNA is an oligonucleotide.

10. The method of claim 1, wherein said nucleic acid is RNA.

11. The method of claim 1, wherein said nucleic acid is from 1–100 nucleotides in length.

12. The method of claim 1, wherein said nucleic acid is from 100–1000 nucleotides in length.

13. The method of claim 1, wherein said nucleic acid is from 1000–10,000 nucleotides in length.

14. The method of claim 1, wherein said nucleic acid is from 10,000–1,000,000 nucleotides in length.

15. A method for isolating nucleic acid, comprising:
   contacting a composition comprising nucleic acid with an effective amount of glycogen to facilitate precipitation of nucleic acid and ethanol in the presence of a carboxylated substrate, wherein said contact results in the association of the nucleic acid with the carboxylated substrate and further wherein the precinitation occurs in the substantial absence of salt.

16. The method of claim 15, wherein said nucleic acid is subsequently eluted from the carboxylated substrate.

17. The method of claim 15, wherein said nucleic acid is DNA.

18. The method of claim 17, wherein the DNA is genomic DNA.

19. The method of claim 17, wherein the DNA is plasmid DNA.

20. The method of claim 17, wherein the DNA is an oligonucleotide.

21. The method of claim 15, wherein said nucleic acid is RNA.

22. The method of claim 15, wherein said nucleic acid is from 1–100 nucleotides in length.

23. The method of claim 15, wherein said nucleic acid is from 100–1000 nucleotides in length.

24. The method of claim 15, wherein said nucleic acid is from 1000–10,000 nucleotides in length.

25. The method of claim 15, wherein said nucleic acid is from 10,000–1,000,000 nucleotides in length.

* * * * *